US00PP25802P2

(12) United States Plant Patent
Osiecki

(10) Patent No.: US PP25,802 P2
(45) Date of Patent: Aug. 11, 2015

(54) ***ALOCASIA* PLANT NAMED 'ALO5'**

(50) Latin Name: ***Alocasia* hybrid**
Varietal Denomination: ALO5

(71) Applicant: Marian Osiecki, Marianna, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 159 days.

(21) Appl. No.: 13/986,604

(22) Filed: May 16, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Alocasia* cultivar named 'ALO5' is disclosed, characterized by medium to large size, very vigorous growth with strong basal shoot production. The new variety has very thick, sagittate leaf blades with veins surrounded with silver shadowing and contrasting light pink petioles with distinctive brown streaks. The new variety is very easy to grow under low and high light conditions and well as low and high temperature conditions and is commercially suitable for 8 to 10 inch pot production from a single tissue culture plantlet. The new variety is an *Alocasia*, typically produced as an ornamental plant.

1 Drawing Sheet

Latin name of the genus and species: *Alocasia* hybrid.
Variety denomination: 'ALO5'.

BACKGROUND OF THE INVENTION

The new cultivar is a product of a planned breeding program. The objectives of the planned breeding program were to develop new *Alocasia* varieties of large size, fast growth, thick leaves, well branching growth habit, suitable for 6 to 10 inch commercial pot production. Additionally, the inventor sought foliage with interesting coloration. The new variety originated from a cross pollination of an unpatented seed parent referred to as 'Aurora' and the pollen parent, an unpatented, unnamed, proprietary variety of *Alocasia lowii*. The crossing was made during May of 2007.

The new variety was discovered by the inventor, Marian Osiecki, a citizen of the US, in October of 2008 in a group of seedlings resulting from the crossing. The new cultivar was found in a commercial greenhouse in Altha, Fla.

Asexual reproduction of the new cultivar 'ALO5' was first performed at a commercial laboratory in Altha, Fla. by tissue culture on Apr. 7, 2009. Subsequent propagation by tissue culture has shown that the unique features of this cultivar are stable and reproduced true to type.

SUMMARY OF THE INVENTION

The cultivar 'ALO5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALO5.' These characteristics in combination distinguish 'ALO5' as a new and distinct *Alocasia* cultivar:

1. Medium to large size, very vigorous, fast growing plants, with strong basal shoot production.
2. Symmetrical growth habit.
3. Dark green, very glossy foliage with veins surrounded by silver shadow.
4. Very thick, closely overlapping, sagittate leaf blades.
5. Attractive, very strong, thick, light pink petioles with distinctive brown streaks.
6. Very easy to grow even under low and high light conditions as well in low and high temperatures.
7. 'ALO5 is suitable for production in 8 to 10" pots from a single tissue culture plantlet.

PARENT COMPARISON

Plants of the new cultivar 'ALO5' are similar to the unpatented seed parent 'Aurora' in most horticultural characteristics. The new variety however differs in the following characteristics:

1. 'ALO5' is a more vigorous and faster growing plant than 'Aurora'.
2. 'ALO5' is a shorter plant, in a 6" pot it is 40 cm tall whereas 'Aurora' is 50-60 cm tall.
3. Plants of 'ALO5' have more symmetrical growth and are larger in diameter than 'Aurora'.
4. The leaf blades of 'ALO5' are darker green, thicker and more glossy than leaf blades of 'Aurora'.
5. Leaf veins of 'ALO5' are thicker, have much darker and broader silver shadow than 'Aurora'.
6. The lower side leaf blade of 'ALO5' is light burgundy and glossy where lower side leaf blade of Aurora' is green and not glossy.
7. Leaf blades of 'ALO5' are oriented facing flatly out, whereas leaf blades of 'Aurora' are oriented downward and nodding.
8. Leaf petioles of 'ALO5' are thicker and stronger compared to petioles of 'Aurora'.

9. Leaf petioles of 'ALO5' are light pink with well marked brown streaks whereas leaf petioles of 'Aurora' are pink with very delicate green streaks.

Plants of the new cultivar 'ALO5' are similar to the pollen parent, an unpatented, unnamed, proprietary variety of *Alocasia lowii*, in most horticultural characteristics. The new variety however differs in the following characteristics:

1. 'ALO5' is a shorter plant, in a 6" pot it is 40 to 50 cm tall in a 6" pot compared to *A. lowii* is 60-70 cm tall.
2. 'ALO5' produces basal shoots more abundantly than *A. lowii.*
3. Plants of 'ALO5' are more symmetrical and narrower in diameter than *A. lowii.*
4. 'ALO5' is fuller and denser than *A. lowii.*
5. The leaf blades of 'ALO5' are smaller and more elongated comparing to the larger, rounder leaf blades of *A. lowii.*
6. Leaf blades of 'ALO5' are thicker, darker green, more glossy and have less silver color between veins than *A. lowii.*
7. Leaf blades of 'ALO5' are have a flat, outward orientation where leaf blades of *A. lowii* are oriented downward and nodding.
8. Leaf petioles of 'ALO5' are shorter and stronger than leaf petioles of *A. lowii.*
9. 'ALO5' leaf petioles are pink with distinctive brown streaks whereas *A. lowii* leaf petioles are light green to green color with green-brown streaks.
10. Leaves of 'ALO5' closely overlap each other whereas leaves of *A. lowii* are spaced.

COMMERCIAL COMPARISON

'ALO5' can be compared to the unpatented commercial variety *Alocasia* 'Polly'. Plants of 'Polly' are similar to plants of 'ALO5' in most horticultural characteristics. However 'ALO5' differs from 'Polly' in the following characteristics:

1. 'ALO5' is a more vigorous, taller and faster growing plant than 'Polly'.
2. 'ALO5' is a wider and less open plant than 'Polly'.
3. Leaf blades of 'ALO5' are thicker, and larger, with more silver color between veins compared to the smaller leaves of 'Polly'.
4. The lower side of 'ALO5' leaf blade is light burgundy whereas the lower leaf blade of 'Polly' is darker burgundy.
5. Leaf blades of 'ALO5' are oriented horizontally whereas leaf blades of 'Polly' are oriented downward and nodding.
6. 'ALO5' leaf petioles are light pink with well marked brown streaks whereas 'Polly' leaf petioles are light green to green color with a few very light green streaks.
7. 'ALO5' is more tolerant to disease and stress conditions than 'Polly'.

'ALO5' can be compared to the unpatented *Alocasia amazonica*. Plants of *Alocasia amazonica* are similar to plants of 'ALO5' in most horticultural characteristics. However 'ALO5' differs from *Alocasia amazonica* in the following characteristics:

1. 'ALO5' is a more vigorous and faster growing plant than *A. amazonica.*
2. 'ALO5' is a fuller plant, with more basal shoots than *A. amazonica.*
3. Plants of 'ALO5' are shorter, less spreading, and denser than plants of *A. amazonica.*
4. Leaves of 'ALO5' closely overlap each other where leaves of *A. amazonica* are spread out.
5. Plants of 'ALO5' are more symmetrical and narrower in diameter than *A. amazonica.*
6. The leaf blades of 'ALO5' are thicker, shorter, with more silver color between veins than *A. amazonica.*
7. The lower side of 'ALO5' leaf blade is light burgundy whereas lower side of *A. amazonica* leaf blade is dark burgundy.
8. 'ALO5' leaf petioles are light pink with distinctive brown streaks, whereas leaf petioles of *A. amazonica* are light green to green color without visible streaks.
9. Leaves of 'ALO5' are oriented horizontally comparing to the downwardly nodding leaves of *A. amazonica.*
10. 'ALO5' is more tolerant to disease and stress conditions than *A. amazonica.*
11. Leaves of 'ALO5' closely overlap each other, whereas leaves of *A. amazonica* are spread out.

'ALO5' can be compared to the commercial variety *Alocasia* 'ALO4' application Ser. No. 13/986,605. Plants of 'ALO4' are similar to plants of 'ALO5' in most horticultural characteristics. However 'ALO5' differs from 'ALO4' in the following characteristics:

1. Plants of 'ALO5' are wider than plants of 'ALO4'. Typically plants of a similar age of 'ALO5' grow to 60 cm in width, whereas similar aged plants of 'AL05' are 42 cm wide.
2. The leaf blade of 'ALO5' is longer, typically having a range from 40 to 50 cm compared to a typical leaf blade length of 28 to 32 cm for 'ALO4'.
3. 2. The leaf blade of 'ALO5' is narrower, typically having a range from 16 to 19 cm compared to a typical leaf blade length of 11 to 14 cm for 'ALO4'.
4. The petiole of 'ALO5' is colored mainly Greyed-Red compared to Greyed-Purple petioles of 'ALO4'.

'ALO5' can be compared to the commercial variety *Alocasia* 'ALO1' application Ser. No. 13/986,613. Plants of 'ALO1' are similar to plants of 'ALO5' in most horticultural characteristics. However 'ALO5' differs from 'ALO1' in the following characteristics:

1. Plants of 'ALO5' are shorter than plants of 'ALO1'. Typically plants of 'ALO5' grow to 45 cm in height, whereas similar aged plants of 'ALO1' are 65 cm tall.
2. The leaf blade of 'ALO5' is longer typically having a range from 40 to 50 cm compared to a typical leaf blade length of 28 to 35 cm for 'ALO1'.
3. The varieties differ in foliage coloration: Mature foliage coloration of 'ALO1' as follows:
   Mature foliage upper side: Near RHS Greyed-Green N189A. Slightly flushing RHS Greyed-Green 190C around veins.
   Mature foliage under side: Near RHS Green 143A, heavily flushed over nearly entire surface RHS Greyed-Purple N186C. Margin RHS Green 143A.

Compared to mature foliage of 'ALO5'
   Mature foliage upper side: Near RHS Green139A, but darker
   Mature foliage under side: Near RHS Greyed-Purple N186C

BRIEF DESCRIPTION OF THE PHOTOGRAPH

The accompanying photograph in FIG. 1 illustrates in full color a typical plant of 'ALO5' grown in a greenhouse in Altha, Fla. This plant is approximately 6 months old, shown in a 6 inch pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'ALO5' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.

Botanical classification: *Alocasia* hybrid 'ALO5'.

PROPAGATION

Root description: Thick, fleshy roots. Roots approximately 0.6 cm thick, colored near RHS White 155A. Rhizomes approximately 0.7 cm thick, colored near RHS White 155A.

PLANT

Growth habit: Rapid, upright. Basal leaves emerge in clumps.

Plant shape: Upright, petioles and leaves slightly arching out. No stems.

Height: Approximately 45 cm to top of foliar plane.

Plant spread: Approximately 60 cm in a 6 inch pot.

Pot size of plant described: 6 inch.

Growth rate: Rapid.

Branching characteristics: No true branching. Leaves emerge direct from base of plant.

Number of clumps of leaves: 1 or 2.

Number of leaves per clump: Average 6 to 12.

Number of leaves per plant: Approximately 6 to 20.

Age of plant described: Approximately 6 months.

FOLIAGE

Leaf:

*Arrangement.*—Single leaves emerging basally.

*Largest, mature, fully expanded leaf.*—Length(excluding petiole): Range from 40 to 50 cm. Width: Range from 16 to 19 cm. Shape of blade: Nearly Hastate, with two very deep lobes that angle upward, rather than outward. Average lobe depth 12 cm. Aspect: Slightly undulating, mainly flat. Very slightly puckered. Apex: Apiculate. Base: Hastate, with 2 very deep lobes. Margin: Entire. Appearance: Upper surface glossy. Lower surface glossy. Texture of top surface: Smooth, slightly puckered. Texture of bottom surface: Smooth. Color: Mature foliage upper side: Near RHS Greyed-Green N189A. Slightly flushing RHS Greyed-Green 190C around veins. Mature foliage under side: Near RHS Green 143A, heavily flushed over nearly entire surface RHS Greyed-Purple N186C. Margin RHS Green 143A.

Venation:

*Type.*—Pinnate.

*Venation coloration upper side.*—Near RHS Greyed-Green 190A. Center vein RHS Greyed-Green 191B.

*Venation coloration under side.*—Near RHS Green 143C.

Petiole:

*Length.*—Approximate range between 35 and 48 cm.

*Width.*—At base: Approximately 1.7 cm. At leaf attachment: Approximately 0.8 cm.

*Color.*—Near RHS Greyed-Red 182D, moderately covered in short stripes near RHS Brown 200A. Near leaf attachment, color changes to RHS Yellow-Green 145B, with no stripes approximately 4.0 to 5.0 cm from attachment point.

*Strength.*—Very strong.

*Texture.*—Glabrous.

*Other.*—Petiole sheath present.

Petiole sheath:

*Length.*—Approximately 6.0 to 12.0 cm.

*Width.*—Approximately 1.5 to 2.5 cm.

*Shape.*—Narrow deltoid.

*Color.*—Near RHS Greyed-Red 181D.

*Texture.*—Glabrous.

Immature foliage:

*Length (excluding petiole).*—Approximately 28 cm.

*Width.*—Approximately 12 cm.

*Shape of blade.*—Sagittate with two very deep lobes that angle upward, rather than outward. Average lobe depth 12 cm.

*Aspect.*—Slightly undulating, mainly flat. Very slightly puckered.

*Apex.*—Apiculate.

*Base.*—Hastate, with 2 very deep lobes.

*Margin.*—Entire.

*Appearance.*—Young foliage upper surface shiny, lower surface matte.

*Texture of top surface.*—Smooth.

*Texture of bottom surface.*—Smooth.

*Color.*—Young foliage upper side: Near RHS Greyed-Green N189A. Some flushing from veins RHS Greyed-Green 190D. Young foliage under side: Near RHS Green 138A with overlay coloration RHS Greyed-Purple N186C.

Immature foliage venation:

*Type.*—Pinnate.

*Venation coloration upper side.*—Near RHS Greyed-Green 191D. Main vein near RHS Greyed-Green 191B.

*Venation coloration under side.*—Near RHS Green 138B.

INFLORESCENCE

Not observed to date.

OTHER CHARACTERISTICS

Disease resistance: Greater resistance than typical of *Alocasia* to *Myrothecium* and leaf *Phytophthora* has been observed.

Drought tolerance and cold tolerance: The new cultivar is a typical *Alocasia*, cold tolerant to approximately 5° to 7° C. and does not tolerate drought.

Fruit/seed production: Not observed.

What is claimed is:

1. A new and distinct cultivar of *Alocasia* plant named 'ALO5' as herein illustrated and described.

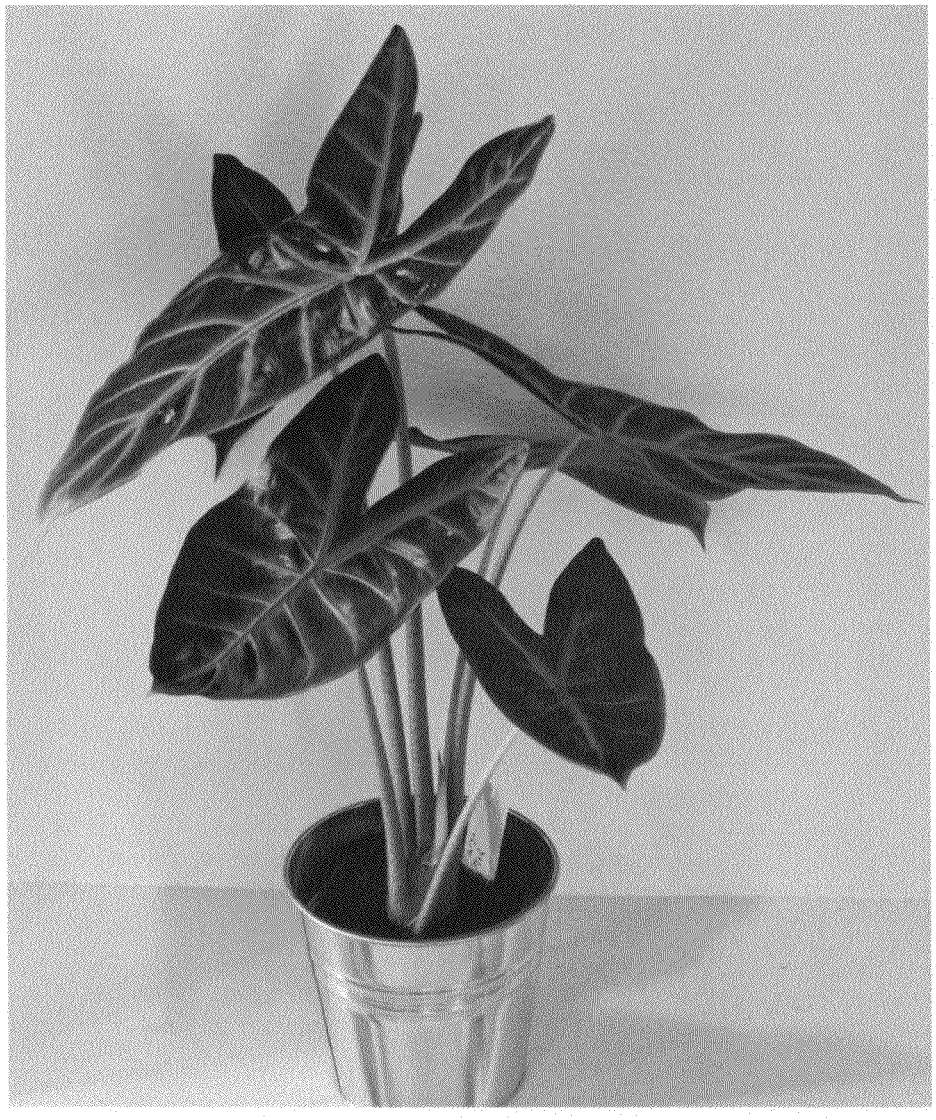

* * * * *